(12) United States Patent
Stenzel

(10) Patent No.: US 7,326,433 B2
(45) Date of Patent: Feb. 5, 2008

(54) METHOD OF CRYOGENICALLY COATING A DEVICE

(75) Inventor: Eric B. Stenzel, Tuam (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/916,105

(22) Filed: Aug. 10, 2004

(65) Prior Publication Data

US 2006/0035011 A1    Feb. 16, 2006

(51) Int. Cl.
*B05D 3/00* (2006.01)
(52) U.S. Cl. ............... 427/2.1; 427/2.24; 427/2.25
(58) Field of Classification Search .................. None
See application file for complete search history.

(56) References Cited

U.S. PATENT DOCUMENTS 6,187,370 B1 * 2/2001 Dinh et al. ............... 427/2.24
6,997,949 B2 * 2/2006 Tuch ........................ 623/1.42

FOREIGN PATENT DOCUMENTS

EP    1216717    *    6/2002

* cited by examiner

*Primary Examiner*—Erma Cameron
(74) *Attorney, Agent, or Firm*—Jones Day

(57) ABSTRACT

The present invention is directed to a method for coating a surface of a medical device with a coating composition. The method involves chilling the surface to be coated to below the freezing point of at least one solvent contained in the composition. This coating composition is applied to the chilled surface, and a portion of the coating composition is allowed to freeze onto the surface. The surface can then be heated (either by the application of heat from an external source, by allowing to heat by ambient air) to above the freezing point of the solvent in the coating composition to allow the solvent to thaw and be removed, thereby forming a smooth, uniform coating on the surface of the medical device.

34 Claims, No Drawings

METHOD OF CRYOGENICALLY COATING A DEVICE

FIELD OF THE INVENTION

The present invention relates generally to implantable medical devices. More specifically the present invention relates to a method for coating a surface of a medical device with a coating composition. The method involves chilling the surface to be coated to a temperature below the freezing point of a solvent contained in the coating composition. This coating composition is applied to the chilled surface, and at least a portion is allowed to freeze onto the surface. The surface can then be heated to above the freezing point of the solvent(s) in the coating composition to first allow the coating composition to thaw and reflow to form a smooth surface. The coated device can then be further processed using heat, optical or particle radiation, radio or microwave emission, application of electrical current through the coated device, freeze drying, or spin drying to thereby remove the desired solvents. The final result is a device that retains a smooth and uniform coating containing the desired components that may include a combination of one or more polymers and/or therapeutic agents.

BACKGROUND OF THE INVENTION

Coatings have been applied to surfaces of medical devices because it is believed that the coatings provide the medical devices with certain advantages. Coatings containing antimicrobial agents have been applied to medical device surfaces to prevent infection. For example, U.S. Pat. No. 6,468,649 to Zhong et al. teaches an implantable medical device having a substrate with a hydrophilic coating composition to limit in vivo colonization of bacteria and fungi. Also, coatings containing therapeutic agents have been applied to stent surfaces because it is believed that such coatings help treat or prevent restenosis. For example, U.S. Pat. No. 6,258,121 to Yang et al. discloses a stent having a polymeric coating for controllably releasing an included active agent such as taxol, to inhibit restenosis following angioplasty.

Various methods are known in the art for coating medical devices. These methods include spraying a coating solution onto a device and then evaporating the solvent, to leave a coating of desired components on the surface of the device. For example, U.S. Pat. No. 6,258,121 to Yang et al. discloses stents that are coated by spraying the solution and then evaporating certain components, thereby leaving a coat of the agent on the surface of the stents. Other methods include dipping the medical device into the solution to be coated., as in U.S. Pat. No. 6,156,373 to Zhong et al. U.S. Pat. No. 6,569,195 to Yang et al. discloses dipping a stent into a mixture comprising a solvent, a polymer, and a therapeutic agent, with subsequent evaporation of the solvent to leave a polymeric coating. Another method that can be used is an electrohydrodynamic coating process described in U.S. Pat. No. 6,669,980 to Hansen where a coating solution is electrically charged, atomized and deposited on the device by an attractive electrostatic force.

However, it has been found in the present invention that the use of cryogenic means to coat medical devices has many advantages that were not known in the art before now.

SUMMARY OF THE INVENTION

The present invention provides a method for coating a surface of a medical device comprising chilling the surface of the medical device; applying a coating composition onto the chilled surface; and allowing at least a portion of the coating composition that is applied to the chilled surface to freeze onto the chilled surface.

This method is preferable over prior methods for several reasons—it provides a more uniform, smooth coating, and the ability to control the temperature makes the method for application easier to control overall. Also, because different components of the coating composition have different known freezing and melting points, the current invention is an advantageous method in which different components can be effectively and reliably applied to the surface, leading to more even distribution of the coating over the medical device that better accomplishes the purposes for which the coated medical device is directed.

In the present invention, the term "medical device" can be used to refer to, without limitation, items such as catheters, stents, endotracheal tubes, hypotubes, filters such as those for embolic protection, surgical instruments and the like. Any device that is typically coated in the medical arts and whose surface is capable of being frozen can be used in the present invention. The present invention is particularly useful in conjunction with local delivery of drugs or therapeutic substances on a stent within the vascular system. The invention may also be utilized in conjunction with drug delivery from balloon catheters or stents for use in other body lumens. The invention is particularly useful when utilizing a water soluble drug or therapeutic substance which tends to dissolve and migrate within a blood or other body fluid environment.

The term "coating composition" refers to any composition that is desired to be deposited upon the surface of a medical device, including those components that are to be later removed through evaporation such as solvents. The components in the coating composition must be able to withstand low temperatures and low pressures or vacuums. Additionally, they must be compatible with each other.

More particularly, the present invention is directed to a method for coating a surface of a medical device with a coating composition comprising chilling the surface of the medical device to a temperature below the freezing point of at least one solvent contained in the coating composition that is to be applied to the surface. The coating composition is then applied onto the chilled surface. Thereafter, at least a portion of the coating composition that is applied to the chilled surface is allowed to freeze onto the surface. The portion that freezes can be any part of the coating composition applied to the surface. The portion that freezes can be a part of the applied coating composition that is nearest or furthest from the surface. The method may further comprise allowing the temperature of the coated surface to increase above the freezing point of the coating composition.

Preferably, the medical device is a stent. The surface of the device can be chilled in a number of ways, including but not limited to: exposing the surface to a chilled gas or convection/conduction cooling. Convection or conduction cooling can be achieved by storing the medical device in a refrigerated environment or by storing, exposing, or dipping the medical device in a chilled liquid such as liquid nitrogen, liquid helium, or liquid oxygen. Liquefied gas is a substance that is a gas at standard temperature and pressure (STP).

The coating composition of the present invention preferably comprises a therapeutic agent and/or a polymeric material. Suitable therapeutic agents include, without limitation, paclitaxel and derivatives and analogues thereof.

The coating composition of the present invention can be applied to the surface of the medical device in a number of ways. The surface of the medical device can be dipped into the coating composition. Alternatively, the coating composition can be applied to the surface of the medical device by spray-coating including electrohydrodynamic spraying or electrostatic spraying. The surface of the medical device can be rotated while the coating composition is applied to the surface. The coated surface can also be spin-dried to drive off any coating composition that is not frozen to the surface.

When the coating composition is applied to the surface of the medical device, it is necessary to control the size or amount of the portion allowed to freeze onto the surface. The size can be controlled in several ways. For instance, the size of the portion of the coating composition that is allowed to freeze onto the surface is controlled by adjusting the amount of one or both of the polymeric or therapeutic agent. Preferably, the size is controlled by monitoring the change in temperature of at least one surface of the device being coated during the deposition process.

The surface of a device, such as a stent, can be chilled to a known temperature "A" that is below the freezing point of at least one solvent in the coating composition, i.e., temperature "B." Temperature "A" can be determined by measuring the resistance or conductivity of the device. As metals become cooler, their resistivity decreases proportionately with the temperature drop. Using a sensitive resistance meter, such as the digital micro-ohmmeter model ZY9858 supplied by Hotec Technologies, Inc., the resistivity of the device can be measured. A change in the electrical resistance can then be used to calculate the change in the temperature of the surface. A change in the temperature of the surface can then be used to determine the quantity of coating composition that should be deposited. Another method of measuring the temperature of the surface is by using a doped crystal that allows temperature changes to be measured from the changes in photoluminescence, Raman spectroscopy, or fluorescence from an applied energy source such as a laser. An additional method of determining the quantity of the solution deposited to the surface would be to attach the surface to a scale during the coating process.

Preferably, the coating composition is chilled to a temperature that is about 10% more than the freezing point of the solvent or other composition component. The temperature of the coated surface can be determined by monitoring the infrared signature of the coated surface or through the use of a temperature probe such as a thermometer or a thermocouple. The amount of coating composition frozen to the surface can also be determined based on the temperature of the coated surface. The temperature of the coated surface may be allowed to increase above the freezing point of the coating composition by exposing the surface to a heat source, for example. Additionally, the temperature of the coated surface may be allowed to increase at a rate such that the coating composition that is frozen onto the surface will form a smooth uniform coating. Preferably, the coating composition is applied to the chilled surface in a manner such that a layer of unfrozen coating composition is disposed over the portion of the coating composition that is allowed to freeze onto the surface.

The present invention is also directed to methods for coating a surface of a medical device with a coating composition comprising chilling the surface of the medical device to a temperature below the freezing point of a solvent contained in the coating composition that are to be applied to the surface. Then the coating composition, which comprises the solvent, a therapeutic agent and a polymeric material, is applied onto the chilled surface, and at least a portion of the coating composition that is applied to the chilled surface is allowed to freeze onto the surface. The temperature of the coated surface is allowed to increase above the freezing point of the solvent. This method may further comprise allowing the temperature of the coated surface to increase to eliminate the solvents from the coating or allowing the pressure around the coated surface to decrease to eliminate the solvents from the coating.

In another preferred embodiment, the present invention is directed to a method for coating a surface of a medical device with a coating composition comprising chilling the surface of the medical device to a temperature below the freezing point of a solvent contained in the coating composition that is to be applied to the surface. Then, the coating composition, which comprises the solvent, a therapeutic agent and a polymeric material, is applied onto the chilled surface; and at least a portion of the coating composition that is applied to the chilled surface is allowed to freeze onto the surface. Thereafter, the temperature of the coated surface is allowed to increase above the freezing point of the solvent temperature at a rate such that the coating composition that is frozen onto the surface will form a smooth uniform coating.

DETAILED DESCRIPTION OF THE INVENTION

In the present invention, the substance(s) to be coated onto the medical device is applied by freezing a composition containing the substance(s) onto the surface of the device instead of applying the composition in its wet or dry form at room temperatures, as is conventional in the art. In the present method, the coating composition is applied in liquid form to a chilled surface of a medical device. Upon application, the coating composition freezes instantaneously onto the surface of the chilled medical device. The temperature of the surface of the medical device is then increased, for example by the application of heat from an external source or by allowing the surface to heat by ambient air. The coating composition is thereby allowed to thaw, reflow, and evaporate, leaving a uniform and smooth coating on the surface of the medical device.

Preferred ways for chilling the medical device surface include, without limitation, dipping the medical device into liquid nitrogen or oxygen, spraying the medical device with a chilled gas such as helium, nitrogen or oxygen, and convection cooling by storing the medical device in a refrigerated environment.

Suitable medical devices that can be used in the present invention include stents, such as vascular stents, catheters, endotracheal tubes, hypotubes, filters such as those for embolic protection, surgical instruments and the like. Any device that is typically coated in the medical arts and is capable of being frozen can be used in the present invention. The medical device preferably includes a body portion having an exterior surface defined thereon with the body portion being expandable from a first position, wherein the body portion is sized for insertion into the vessel lumen, to a second position, wherein at least a portion of the exterior surface of the medical device is in contact with the lumen wall.

Preferably, the coating solution comprises a solvent, a polymeric material, and a therapeutic agent with subsequent evaporation of the solvent to leave a therapeutic agent and polymeric coating.

Preferred solvents include organic solvents such as toluene, tetrahydrofuran (THF), chloroform, toluene, acetone, isooctane, 1,1,1-trichloroethane, dichloromethane, dimethyl acetamide (DMAC), methyl ethyl ketone and mixtures thereof. The skilled artisan would be aware of which solvents are suitable for preparing the coating compositions. Also, it should be noted that all constituents of the coating composition need not be dissolved in the solvent. For example, solids that are insoluble in a particular solvent may be introduced into the solvent and remain solid such that the solvent carries the compound to the device where the solids become trapped on the device in the frozen solvents.

The term "therapeutic agent" as used in the present invention encompasses drugs, genetic materials, and biological materials and can be used interchangeably with "biologically active material". Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti-thrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, taxol, paclitaxel, 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl)glutamine, 2'-O-ester with N-(dimethylaminoethyl)glutamide hydrochloride salt, nitroglycerin, nitrous oxides, nitric oxides, antibiotics, aspirins, digitalis, estrogen, estradiol and glycosides. In one embodiment, the therapeutic agent is a smooth muscle cell inhibitor or antibiotic. In a preferred embodiment, the therapeutic agent is taxol (e.g., Taxol®), or its analogs or derivatives. In another preferred embodiment, the therapeutic agent is paclitaxel, or its analogs or derivatives. In yet another preferred embodiment, the therapeutic agent is an antibiotic such as erythromycin, amphotericin, rapamycin, adriamycin, etc.

The term "genetic materials" means DNA or RNA, including, without limitation, of DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:
anti-thrombogenic agents such as heparin, heparin derivatives, urokinase, and PPack (dextrophenylalanine proline arginine chloromethylketone);
anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;
anti-inflammatory agents such as glucocorticoids, betamethasone, dexamethasone, prednisolone, corticosterone, budesonide, estrogen, sulfasalazine, rosiglitazone, mycophenolic acid and mesalamine;
anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives;
anesthetic agents such as lidocaine, bupivacaine, and ropivacaine;
anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;

DNA demethylating drugs such as 5-azacytidine, which is also categorized as a RNA or DNA metabolite that inhibit cell growth and induce apoptosis in certain cancer cells;

vascular cell growth promoters such as growth factors, vascular endothelial growth factors (VEGF, all types including VEGF-2), growth factor receptors, transcriptional activators, and translational promoters;

vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents, vasodilating agents, and agents which interfere with endogenous vasoactive mechanisms;

anti-oxidants, such as probucol;

antibiotic agents, such as penicillin, cefoxitin, oxacillin, tobranycin, rapamycin (sirolimus);

angiogenic substances, such as acidic and basic fibroblast growth factors, estrogen including estradiol (E2), estriol (E3) and 17-beta estradiol;

drugs for heart failure, such as digoxin, beta-blockers, angiotensin-converting enzyme (ACE) inhibitors including captopril and enalopril, statins and related compounds; and macrolides such as sirolimus or everolimus.

Preferred biological materials include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl)glutamine, and 2'-O-ester with N-(dimethylaminoethyl) glutamide hydrochloride salt.

Other suitable therapeutic agents include tacrolimus, halofuginone, inhibitors of HSP90 heat shock proteins such as geldanamycin, microtubule stabilizing agents such as epothilone D, phosphodiesterase inhibitors such as cliostazole.

Other preferred therapeutic agents include nitroglycerin, nitrous oxides, nitric oxides, aspirins, digitalis, estrogen derivatives such as estradiol and glycosides.

In one embodiment, the therapeutic agent is capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In another embodiment, the therapeutic agent is capable of inhibiting cell proliferation and/or migration.

In certain embodiments, the therapeutic agents for use in the medical devices of the present invention can be synthesized by methods well known to one skilled in the art. Alternatively, the therapeutic agents can be purchased from chemical and pharmaceutical companies.

The polymeric material should be a material that is biocompatible and avoids irritation to body tissue. Preferably the polymeric materials used in the coating composition of the present invention are selected from the following: polyurethanes, silicones (e.g., polysiloxanes and substituted polysiloxanes), and polyesters. Also preferable as a polymeric material is styrene-isobutylene-styrene (SIBS). Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing.

In a preferred embodiment of the presently claimed method, the first step comprises chilling the medical device to below the freezing point of at least one solvent in the coating composition to be coated onto the device. The second step comprises applying the coating composition to the chilled device such that at least a portion of the coating composition adheres to the chilled device and remains in the frozen solid phase. This can be done in a number of ways, including, without limitation, spraying with an atomized spray of the coating composition that instantly freezes to the device upon contact, pouring the coating composition onto the surface of the device, or dipping the device into a bath of the coating composition that subsequently freezes to the device upon contact. In a preferred embodiment, the method includes a step comprising slowly heating the chilled device and allowing the warming to melt the frozen coating composition at a rate sufficient to allow the solvent in the coating composition to thaw and reflow to form a liquid layer and to then evaporate, leaving behind the desired coating and thereby providing a smooth surface and uniform coating on the medical device. Preferably, the coating composition is allowed to warm to a temperature that is about 10% higher than the freezing point of the solvent.

In another embodiment, the method includes a step comprising placing the coated device in a chamber where the atmospheric pressure is reduced such that at least one solvent component is allowed to evaporate without going through its liquid state first. This process would provide a method for the frozen solvents to phase change from a solid to a gas and not allow for a solvent thawing and reflow process.

The coating composition should freeze to the medical device in a uniform layer immediately upon contact. This result can be ensured by controlling a number of variables, including the temperature at which the medical device is maintained while the coating composition is being applied, the density of the coating composition and its components, such as the therapeutic agent and/or polymeric material and the time allowed for the coating composition and medical device to be in contact with one another before evaporation of the components of the coating composition that are not desired to remain deposited upon the surface of the medical device. For example, one of ordinary skill in the art can appreciate that different components of the coating composition will have different freezing and melting temperatures, and that the temperature, concentration and other parameters can be varied such that certain components will evaporate while other components are left coated to the surface of the medical device. This method can even be repeated, so that the device is coated with a plurality of layers, all having different concentrations of components.

For example, it has been shown that a very cold medical device surface will ensure that more of the coating composition will freeze to the surface, thereby forming a thicker coating. Maximizing the variables that ensure a uniform evaporation and smooth coating on the surface of the device is a main object of the present invention.

In one preferred embodiment of the present invention, the medical device is cooled to just below the freezing point of the coating composition, and maintained at that temperature while the coating composition is applied to its surface. This embodiment provides a way of coating the medical device that is efficient from an energy standpoint, using the least amount of energy necessary to bring the medical device to a point below freezing of the coating composition, thereby accomplishing the objectives of the invention in the most efficient manner possible.

Further, during application of the coating composition, the surface of the medical device can be rotated or moved, causing some of the coating composition to freeze to the surface before additional amounts of the coating composition are applied and frozen to the surface. This is advantageous when it is desired to coat two or more different coating compositions to the surface of the medical device—for example, if it is desired that the patient is treated by the administration of different drugs in different stages, to be released into the body of the patient in varying stages.

In addition to, or instead of heating the coated medical device after freezing, of the portion with coating composition the device can be freeze-dried or spin-dried. In freeze-drying, the device is freeze coated as described above and allowed to thaw out to smooth the surface of the coating, but then is frozen again and subjected to a vacuum to provide the proper pressure, volume and temperature to maintain the solvent in vapor phase. In spin-drying, the coated medical device is subjected to spinning at a velocity optimal to maintain the uniformly dry, smooth coating. When spin drying the coated device, the temperature of the device can be controlled to allow for selected solvent components of the coating to be removed. For example, the coated device can be kept at a temperature where one solvent component 'A' remains a solid (i.e. frozen) while solvent component 'B' phase changes to a liquid. Spin drying would remove solvent component 'B' while leaving solvent component 'A' still attached to the device as a solid. For these methods, by maintaining the proper conditions, the solvent can be transformed from solid (frozen) phase directly to vapor (evaporated) phase without passing through a liquid phase. This is an advantageous step that ensures a smoother phase transition for the coating solution, as well as a more uniform coating. Those skilled in the art will appreciate that by ensuring that the coating solution skips the liquid phase, the disadvantages of staggered phase changes, and the accompanying lack of uniformity in the coating, will be avoided.

In another preferred embodiment of the present invention, the medical device is cooled to far below the freezing temperature of the coating composition, so that when the coating composition is applied to the surface of the medical device, the coating composition freezes. The temperature is slowly warmed over a greater temperature range in order to reach the point at which the solvent in the coating composition will evaporate from the surface of the medical device. This can be done either by allowing the medical device surface to warm slowly, or by heating it slowly with external means until it has reached the desired higher temperature. It has been shown that warming the frozen device incrementally uses more energy, but is advantageous in that it provides a much more uniform and smooth coating on the surface of the device, for the same reasons as stated above—slowly increasing the temperature prevents staggered temperature changes for different particles, and a more uniform outcome. Certain applications for this process may require an extremely uniform coating that can be achieved with more predictability and accuracy when the device surface is frozen to far below the freezing point of the coating composition and allowed to heat incrementally.

Preferably, the temperature of the surface of the medical device is monitored in order to determine how much coating composition is frozen on the surface at any given time. Most preferably, the monitoring is accomplished by monitoring the resistivity of the device surface or device where a small electrical voltage is passed through the device during the coating process. The resistivity of the device is monitored by a sensitive resistance meter, such as the digital micro-ohmmeter model ZY9858 supplied by Hotec Technologies, Inc. As the coating composition is deposited, the chilled device surface begins to warm at a rate consistent with the energy transferred from the coating composition to the device surface.

As the device warms, the resistivity of the device or device surface will increase and can be measured by the precision ohmmeter. By knowing the initial temperature of the device or device surface, the temperature and heat capacity of the coating composition, the quantity of coating composition that has become attached to the device can be calculated.

In another embodiment, a temperature sensor can be placed near the device as it is coated. The temperature sensor is chilled as is the device surface to be coated and exposed to the sprayed coating. By monitoring the effect on the temperature sensor, the amount of deposited coating composition can be calculated as above. Examples of temperature sensors include, but are not limited to, resistive thermal devices, capacitive thermal devices, or a semiconductor junction such as a diode or a transistor.

In yet another embodiment, a crystal material that is doped with $Cr^{3+}$ such as $Ruby(Cr:Al_2O_3)$, is placed near the device as detailed above. The temperature of this crystal is measured by directing a laser onto the crystal and measuring the photoluminescence, Raman spectrum, fluorescence, or fluorescence lifetime. Differences in the temperature can be detected by changes to this spectrum.

It will be appreciated by those skilled in the art that while the invention has been described above in connection with particular embodiments, the invention is not necessarily so limited and that numerous other embodiments, examples, uses, modifications and departures from the embodiments described herein may be made without departing form the inventive concept. Also, all the references mentioned herein are incorporated by reference for all purposes.

I claim:
1. A method for coating a surface of a medical device with a coating composition comprising the steps of:
   (a) chilling the surface of the medical device to a temperature below the freezing point of at least one solvent contained in the coating composition;
   (b) applying the coating composition onto the surface while the surface is chilled; and
   (c) allowing at least a portion of the coating composition that is applied to the chilled surface to freeze onto the chilled surface.
2. The method of claim 1, wherein the medical device is a stent.
3. The method of claim 1, wherein the surface is chilled by exposing the surface to a super-chilled gas.
4. The method of claim 1, wherein the surface is chilled by exposing the surface to a chilled gas.
5. The method of claim 4, wherein the chilled gas comprises liquid helium, liquid oxygen or liquid nitrogen.
6. The method of claim 1, wherein the surface is chilled by convection cooling.
7. The method of claim 1, wherein the coating composition comprises a therapeutic agent.
8. The method of claim 7, wherein the therapeutic agent comprises paclitaxel, a derivative of paclitaxel or an analogue of paclitaxel.
9. The method of claim 7, wherein the therapeutic agent comprises sirolimus, everolimus, or tacrolimus.
10. The method of claim 1, wherein the coating composition comprises a polymeric material.
11. The method of claim 10, wherein the coating composition further comprises a therapeutic agent.
12. The method of claim 1, wherein the coating composition is applied to the surface by dipping the surface into the coating composition.
13. The method of claim 1, wherein the coating composition is applied to the surface by spray-coating.
14. The method of claim 1, wherein the coating composition is applied to the surface by electrohydrodynamic spraying.
15. The method of claim 1, wherein the size of the portion of the coating composition that is allowed to freeze onto the surface is controlled by monitoring the temperature to which the surface is chilled.
16. The method of claim 1, wherein the size of the portion of the coating composition that is allowed to freeze onto the surface is controlled by monitoring the temperature of the surface using a temperature sensor near the device surface.
17. The method of claim 16, wherein the temperature of the surface is monitored by measuring the resistivity or conductivity of the device.
18. The method of claim 16, wherein the temperature of the surface is monitored by using a resistive thermal device.
19. The method of claim 16, wherein the temperature of the surface is monitored by using a doped crystal that allows temperature changes to be measured from the changes in photoluminescence, Raman spectroscopy, or fluorescence from an applied energy source.
20. The method of claim 19, wherein the applied energy source comprises a laser.
21. The method of claim 11, wherein the size of the portion of the coating composition that is allowed to freeze onto the surface is controlled by adjusting the amount of one or both of the polymeric material or therapeutic agent.

22. The method of claim 1, wherein the coating composition is applied to the chilled surface in a manner such that a layer of unfrozen coating composition is disposed over the portion of the coating composition that is allowed to freeze onto the surface.
23. The method of claim 1 further comprising allowing the coating composition that is frozen onto the surface, to warm to a temperature that is about 10% higher than the freezing point of the solvent.
24. The method of claim 1, wherein the surface is rotated while the coating composition is applied to the surface.
25. The method of claim 1, wherein the coating composition has a freezing point, and wherein the method further comprises allowing the temperature of the coated surface to increase above the freezing point of the coating composition that is frozen onto the surface.
26. The method of claim 21, wherein the coating composition has a freezing point, and wherein the temperature of the coated surface is allowed to reach the temperature that is about 10% higher than the freezing point of the coating composition that is frozen onto the surface, by exposing the surface to a heat source.
27. The method of claim 21, wherein the temperature of the coated surface is allowed to increase at a rate such that the portion of coating composition that is frozen onto the surface will form a smooth uniform coating.
28. The method of claim 1 further comprising spin-drying the coated surface to remove any coating composition that is not frozen to the surface.
29. The method of claim 21, wherein the coating composition further comprises a solvent, and wherein the method further comprises (d) allowing the temperature of the coated surface to increase above the freezing point of the solvent and (e) exposing the coated surface to a vacuum source to vaporize or sublime the solvent.
30. The method of claim 1 further comprising monitoring the infrared signature of the coated surface to determine the temperature of the coated surface.
31. A method for coating a surface of a medical device with a coating composition comprising the steps of:
   (a) chilling the surface of the medical device to a temperature below the freezing point of at least one solvent contained in the coating composition that is to be applied to the surface;
   (b) applying the coating composition, comprising the solvent, a therapeutic agent and a polymeric material, onto the surface while the surface is chilled;
   (c) allowing at least a portion of the coating composition that is applied to the chilled surface to freeze onto the surface; and
   (d) allowing the temperature of the coated surface to increase above the freezing point of the solvent.
32. The method of claim 31 wherein step (d) further comprises allowing the temperature of the coated surface to increase to eliminate the solvent from the coating.
33. The method of claim 31 further comprising allowing the pressure around the coated surface to decrease to eliminate the solvents from the coating.
34. A method for coating a surface of a medical device with a coating composition comprising the steps of:
   (a) chilling the surface of the medical device to a temperature below the freezing point of at least one solvent contained in the coating composition that is to be applied to the surface;
   (b) applying the coating composition, which comprises the solvent, a therapeutic agent and a polymeric material, onto the surface while the surface is chilled;

(c) allowing at least a portion of the coating composition that is applied to the chilled surface to freeze onto the surface; and allowing the temperature of the coated surface to increase above the freezing point of the solvent at a rate such that the portion of coating composition that is frozen onto the surface will form a smooth uniform coating.

* * * * *